United States Patent [19]

Birtwistle et al.

[11] Patent Number: 5,180,579
[45] Date of Patent: Jan. 19, 1993

[54] TOPICAL COMPOSITION COMPRISING A MIXTURE OF PARTICULAR DI-ALKYL OR ALKENYL PHOSPHATE ESTERS AND MONO-ALKYL OR ALKENYL PHOSPHATE ESTERS

[75] Inventors: David H. Birtwistle; Peter Cartere; David A. Rosser, all of Merseyside, England

[73] Assignee: Chesebrough-Pond's USA Co., division of Conopco, Inc., New York, N.Y.

[21] Appl. No.: 768,480

[22] Filed: Sep. 27, 1991

Related U.S. Application Data

[63] Continuation of Ser. No. 442,963, Nov. 29, 1989, abandoned.

[30] Foreign Application Priority Data

Dec. 1, 1988 [GB] United Kingdom ............ 8828017

[51] Int. Cl.$^5$ .............................. A61K 7/06
[52] U.S. Cl. ................... 424/70; 424/57; 424/69; 424/401
[58] Field of Search ........... 514/772, 944, 975; 252/DIG. 14, DIG. 16, DIG. 17, DIG. 5, DIG. 13, 174.16, 174.21, 174.22; 424/70, 47, 57, 69

[56] References Cited

U.S. PATENT DOCUMENTS

| | | | |
|---|---|---|---|
| 2,758,093 | 8/1956 | Ernst | 252/DIG. 17 |
| 4,139,485 | 2/1979 | Imokawa et al. | 252/135 |
| 4,526,710 | 7/1985 | Fujisawa et al. | 252/545 |
| 4,758,376 | 7/1988 | Hirota et al. | 252/545 |

FOREIGN PATENT DOCUMENTS

| | | |
|---|---|---|
| 0018717 | 11/1980 | European Pat. Off. |
| 0077920 | 5/1983 | European Pat. Off. |
| 0224796 | 6/1987 | European Pat. Off. |
| 0321786 | 6/1989 | European Pat. Off. |
| 8901023 | 2/1989 | PCT Int'l Appl. |

Primary Examiner—Thurman K. Page
Assistant Examiner—D. Colucci
Attorney, Agent, or Firm—Milton L. Honig

[57] ABSTRACT

A composition suitable for topical application to the skin or hair, comprises:

a. a short chain dialkyl or dialkenyl phosphate salt having the structure (1):

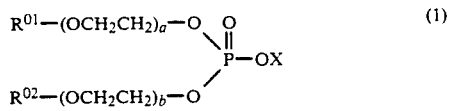

and b. a monoalkyl or monoalkyl phosphate salt (or mixtures thereof), having the structure (2):

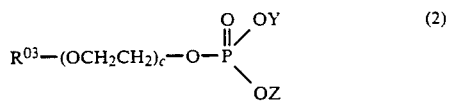

where $R^{01}$ and $R^{02}$ are each chosen from branched or unbranched alkyl or alkenyl groups having an average of from 7 to 9 carbon atoms;

$R^{03}$ is chosen from branched or unbranched alkyl or alkenyl groups having an average of from 6 to 18 carbon atoms;

X, Y and Z are each chosen from H, alkali metal, ammonium and substituted ammonium counterions; and a, b and c are each chosen from 0, or a value of from 1 to 4.

21 Claims, No Drawings

TOPICAL COMPOSITION COMPRISING A MIXTURE OF PARTICULAR DI-ALKYL OR ALKENYL PHOSPHATE ESTERS AND MONO-ALKYL OR ALKENYL PHOSPHATE ESTERS

This is a continuation application of Ser. No. 07/442,963, filed Nov. 29, 1989, now abandoned.

FIELD OF THE INVENTION

The invention relates to compositions suitable for topical application to the skin, (including the mucosae), and to the hair. In particular, the invention is concerned with highly improved detergent compositions suitable for cleansing the whole body surface, including the mouth.

BACKGROUND TO THE INVENTION & PRIOR ART

The damaging effect of conventional detergents used to wash the body surface, particularly where young, tender or damaged skin is involved, has been the subject of intense study for many years in a search for milder-to-the-skin products, which not only cleanse the skin efficiently, but also leave the skin with a pleasant smooth silky feel after the skin surface has been dried off.

The use of certain mono- and di-alkyl phosphate salts for this purpose has been advocated in view of their mild characteristics, but some of this group of salts are used as antifoam agents because of their lather suppressant properties, and would therefore require careful formulation if lather control is not required.

To this end, U.S. Pat. No. 4,139,485 (Kao Soap Co. Ltd.) describes a detergent composition having low irritation properties on human skin, wherein the surfactant component is dialkyl or dialkenyl phosphate salt (DAP) and/or monoalkyl or monoalkenyl phosphate salt (MAP), each alkyl or alkenyl group having from 10 to 16 carbon atoms), the weight ratio of 'DAP' to 'MAP' being from 20:80 to 0:100. This system is stated to possess good detergency.

Also, U.S. Pat. No. 4,526,710 (Kao Corporation), report a study to improve properties of detergent composition which make use of anionic phosphate surface active agents, which Kao maintain are highly innoxious and particularly mild to the skin. As a result, Kao have found that when phosphate ester salts having a specific ion pair, notably mono- or di-alkyl (C8-18) phosphates, are used in combination with alkanol amine salts of higher fatty acids and alkyl amine oxides, the detergency and foaming characteristics are remarkably improved.

Also, U.S. Pat. No. 4,758,376 (Kao) discloses an alternative composition, comprising an alkanolamine salt of a mono or dialkyl (C8-18) phosphate or mixtures thereof, to that described in U.S. Pat. No. 4,526,710 in which the problem of poor foaming due to the dialkyl phosphate salt is dealt with by incorporating with the phosphate a compound chosen from an amidoamine amphoteric surfactant or hydroxysulphobetaine, or an aliphatic lactylate or glycolate.

It is clear from a study of the three Kao references, that all the evidence on which their disclosures are based is restricted to alkyl phosphates or dialkyl phosphates in which the alkyl group has at least 10 carbon atoms. There is absolutely no reference at all to any evaluation of an alkyl phosphate ester or dialkyl phosphate ester salt where the alkyl group or groups contains only 9 carbon atoms, or less.

While investigating Kao's teaching further, particularly their stipulation in U.S. Pat. No. 4,139,485 that the weight ratio of mono- to di-alkyl phosphate salt cannot fall below 80:20, without loss of foaming power. Applicants have now discovered that a greater proportion by weight of the dialkyl phosphate salt of Kao can be tolerated without significant loss of lather volume, provided there is also present a dioctyl phosphate salt. The compositions so obtained are accordingly capable of producing a superior lather volume and an outstanding lather creaminess. Also, the composition is so mild to the skin that it can safely be used for cleansing the mucosae, such as the mouth and the vagina, and other more delicate skin areas. It can also be used in shampoos for frequent, e.g. daily, hair washing, without risk of scalp irritation or damage attributable to harsher products. In addition to these excellent attributes, the ease of rinsing from hair or skin and superior silky-smooth after-use skin feel properties of the compositions, including freedom from skin roughness and erythema, have great consumer appeal.

DEFINITION OF THE INVENTION

Accordingly, the invention provides a composition suitable for topical application to the skin or hair, which comprises:

(a) from 1 to 99% by weight of a short chain dialkyl or dialkenyl phosphate salt (or mixtures thereof) having the structure (1):

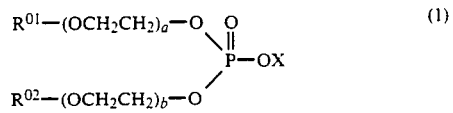

(b) from 1 to 99% by weight of a monoalkyl or monoalkenyl phosphate salt (or mixtures thereof) having the structure (2):

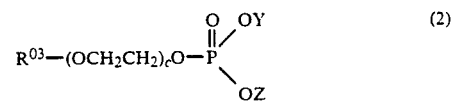

where
$R^{01}$ and $R^{02}$ are each chosen from branched or unbranched alkyl or alkenyl groups having an average of from 7 to 9 carbon atoms;
$R^{03}$ is chosen from branched or unbranched alkyl or alkenyl groups having an average of from 6 to 18 carbon atoms;
X, Y and Z are each chosen from H, alkali metal, ammonium and substituted ammonium counterions; and
a, b and c are each chosen from 0 or a value of from 1 to 4.

DISCLOSURE OF THE INVENTION

The Short Chain Dialkyl or Dialkenyl Phosphate Salt

The composition according to the invention comprises as a surfactant, a short chain dialkyl or dialkenyl phosphate salt (or mixtures thereof) having the structure:

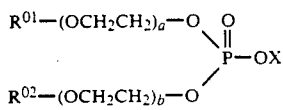

where
- $R^{01}$ and $R^{02}$ are each chosen from branched or unbranched alkyl or alkenyl groups having an average of from 7 to 9 carbon atoms; and
- X is chosen from H, alkali metal ammonium and substituted ammonium counterions;
- a & b are each chosen from 0 or a value of from 1 to 4.

Examples of the dialkyl- and dialkenyl phosphate moiety include:
di-n-heptyl phosphate
di-n-octyl phosphate
di-n-nonyl phosphate
di-(diethyleneglycol-mono-n-nonyl ether) phosphate
di-(ethyleneglycol-mono-n-octyl ether) phosphate
di-n-heptenyl phosphate
di-n-octenyl phosphate
di-n-nonenyl phosphate
di-(triethyleneglycol-mono-n-octenyl ether) phosphate
di-(ethyleneglycol-mono-n-heptyl ether) phosphate
di-(7-methyloctyl) phosphate
di-(5-methylhexyl) phosphate
di-(6,6-dimethylheptyl) phosphate
n-hexyl-n-nonyl phosphate, and
n-hexyl-n-octyl phosphate.

The preferred dialkyl phosphate moiety is di-n-octyl phosphate, and the preferred counterion is chosen from sodium, potassium and triethanolammonium.

The amount of short chain dialkyl or dialkenyl phosphate salt which is present in the composition according to the invention is from 1 to 99%, preferably from 2 to 50% by weight of the composition.

Compositions containing less than 1% by weight of the short chain dialkyl or dialkenyl phosphate salt show poor lather characteristics and lack the desired feel properties associated with compositions containing higher levels of this ingredient.

The Monoalkyl or Monoalkenyl Phosphate Salt

The composition according to the invention also comprises, as a lather modifier, a monoalkyl or monoalkenyl phosphate salt (or mixtures thereof) having the structure (2):

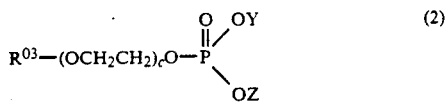

where
- $R^{03}$ is chosen from branched or unbranched alkyl or alkenyl groups having from 6 to 18 carbon atoms;
- Y and Z are each chosen from H, alkali metal, ammonium and substituted ammonium counterions;
- c is chosen from 0 or a value of from 1 to 4.

Examples of the monoalkyl and monoalkenyl phosphate moiety include:
mono-n-hexyl phosphate
mono-n-heptyl phosphate
mono-n-octyl phosphate
mono-n-nonyl phosphate
mono-n-decyl phosphate
mono-n-dodecyl phosphate (mono-lauryl phosphate)
mono-n-tetradecyl phosphate (monomyristyl phosphate)
mono-n-hexadecyl phosphate
mono-n-octadecyl phosphate
mono-(diethyleneglycol-mono-n-nonyl ether) phosphate
mono-(ethyleneglycol-mono-n-octyl ether) phosphate
mono-n-hexenyl phosphate
mono-n-heptenyl phosphate
mono-n-octenyl phosphate
mono-n-nonenyl phosphate
mono-n-dodecenyl phosphate
mono-(triethyleneglycol-mono-n-octenyl ether) phosphate
mono-(ethyleneglycol-mono-n-heptenyl ether) phosphate
mono-7-methyloctyl phosphate
mono-5-methylhexyl phosphate
mono-6,6-dimethylheptyl phosphate
mono-(ethyleneglycol-mono-n-octadecyl ether) phosphate
mono-(diethyleneglycol-mono-n-octadecenyl ether) phosphate
mono-(polyethyleneglycol[5EO]-monooleyl ether) phosphate
mono-(polyethyleneglycol[3EO]-monolauryl ether) phosphate Preferably, the $R^2$ group is lauryl ($C_{12}$); thus when the dialkylphosphate salt is a dioctyl phosphate salt, then the monoalkyl phosphate salt is preferably a monolauryl phosphate salt.

The amount of the monoalkyl or monoalkenyl phosphate salt which is present in the composition according to the invention is from 1 to 99%, preferably from 2 to 50% by weight of the composition.

The choice of an amount of the monoalkyl or monoalkenyl salt within the stated range will modify the lather, in terms of its volume and/or creaminess, that the composition is capable of producing. Evidence is given later in this specification to illustrate how the lather characteristics of the composition can be modified by varying the amounts of the "mono- and di-" phosphate salts that are present.

The Long Chain Dialkyl or Dialkenyl Phosphate Salt

The composition according to the invention can also optionally comprise a long chain dialkyl or dialkenyl phosphate salt (or mixtures thereof) having the structure (30):

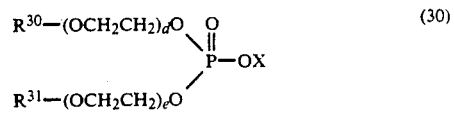

where
- $R^{30}$ and $R^{31}$ are each chosen from branched or unbranched alkyl or alkenyl groups having an average of from 10 to 18 carbon atoms;
- X is chosen from H, alkali metal ammonium and substituted ammonium counterions;
- d and e are each chosen from 0 or a value of from 1 to 10.

Examples of long chain dialkyl and dialkenyl phosphate moiety include:

di-n-decyl phosphate
di-n-dodecyl phosphate (dilauryl phosphate)
di-n-tetradecyl phosphate (dimyristyl phosphate)
di-n-hexadecyl phosphate
di-n-octadecyl phosphate
di-n-dodecenyl phosphate
di-(ethyleneglycol-mono-n-octadecenyl ether) phosphate
di-(diethyleneglycol-mono-n-octadecenyl ether) phosphate
di-(polyethyleneglycol[5EO]-monooleyl ether) phosphate
di-(polyethyleneglycol[3EO]-monolauryl ether) phosphate The preferred long chain dialkyl phosphate salt, when present, is triethanolammonium dilauryl phosphate.

The amount of the long chain dialkyl or dialkenyl phosphate salt, when present, is up to 20%, preferably from 1 to 10% by weight, of the composition.

The weight ratio of the monoalkyl or monoalkenyl phosphate salt to the long chain dialkyl phosphate or dialkenyl salt is from 100:0 to 50:50, preferably 95:5 to 75:25.

Water

The composition according to the invention also comprises an amount of water to act as a vehicle for the mono- and di-alkyl or -alkenyl phosphate salts and to enable them to be provided at a concentration suitable for convenient topical application to human skin.

The amount of water present in the composition of the invention is accordingly up to 99%, preferably from 5 to 99% by weight of the composition.

Co-surfactant

The composition according to the invention can also optionally comprise a co-surfactant, further to modify the surfactant properties attributable to the mono- and di-alkyl or -alkenyl phosphate salts.

Examples of co-surfactants include anionic surfactants other than the phosphate salts defined herein, as well as nonionic, amphoteric and zwitterionic surfactants.

Anionic Co-surfactants

Particularly preferred co-surfactants, when employed, are anionic surfactants, examples of which are set out hereinafter.

i. Fatty acid soap co-surfactant

The composition according to the invention can optionally comprise, as a co-surfactant one or more soaps which are water-soluble or water-dispersable alkali metal salts of an organic acid, especially a sodium or a potassium salt, or the corresponding ammonium or substituted ammonium salt. Examples of suitable organic acids are natural or synthetic alkanoic acids having from 10 to 22 carbon atoms, especially the fatty acids of triglyceride oils such as tallow and coconut oil.

For solid products, such as powders, bars or tablets, the preferred soap is a soap of tallow fatty acids, that is fatty acids derived from tallow class fats, for example beef tallow, mutton tallow, lard, palm oil and some vegetable butters. Minor amounts of up to about 30%, preferably 10 to 20%, by weight of sodium soaps of nut oil fatty acids derived from nut oils, for example coconut oil and palm kernel oil, may be admixed with the sodium tallow soaps, to improve their lathering and solubility characteristics if desired. Whereas tallow fatty acids are predominantel $C_{14}$ and $C_{18}$ fatty acids, the nut oil fatty acids are of shorter chain length and are predominantly $C_{10}$-$C_{14}$ fatty acids.

For liquid or gel products, the preferred soaps are predominantel $C_{10-14}$ fatty acids derived from nut oils, or alternatively, from synthetic alkanoic acids.

The soaps can be provided as a preformed ingredient for the composition, or they can be formed in situ during the manufacture of the composition by reaction of suitable fatty acids and an alkali.

The amount of fatty acid soap which can be present in the composition according to the invention is up to 90%, preferably from 2 to 80% by weight of the composition.

ii. Non-soap anionic co-surfactants

The composition according to the invention can also optionally comprise one or more non-soap anionic co-surfactants, examples of which include:

The alkali metal salts of organic sulphuric reaction products having an alkyl or acyl radical containing from 8–22 carbon atoms and a sulphonic acid or sulphuric acid ester group. Specific examples of these synthetic anionic surfactants are the sodium, ammonium, potassium or triethanolmmonium alkyl sulphates, especially those obtained by sulphating the higher alcohols ($C_8$-$C_{18}$), sodium coconut oil fatty acid monoglyceride sulphates and sulphonates; sodium or potassium salts of sulphuric esters of the reaction product of one mole of a higher fatty alcohol (e.g. tallow or coconut oil alcohols) and 1-12 moles of ethyleneoxide; sodium or potassium salts of alkyl phenol ethylene oxide ether sulphate with 1-10 units of ethylene oxide per molecule and in which the alkyl group contains from 8 to 12 carbon atoms, sodium alkyl glyceryl ether sulphonates, the reaction product of fatty acids having from 10 to 22 carbon atoms esterified with isethionic acid and neutralised with sodium hydroxide; water soluble salts of condensation products of fatty acids with N-methyl taurine. Especially preferred non-soap anionic co-surfactants include:

alkylaryl sulphonates, such as sodium alkyl benzene sulphonate (e.g. TEEPOL CM44, available from Shell).

alkyl sulphates, such as sodium lauryl sulphate (e.g. EMPICOL CX, available from Albright & Wilson), and triethanolomine lauryl sulphate (e.g. EMPICOL TL40/T, available from Albright & Wilson).

alkylether sulphates, such as sodium lauryl ether sulphate (e.g. EMPICOL ESB70, available from Albright & Wilson).

alkyl sulphonates, such as sodium alkane (C13–18) sulphonate (e.g. HOSTAPUR SAS 30, available from Hoechst).

olefin sulphonates, such as sodium olefin sulphonate (C15–18) (e.g. HOSTAPUR OS, available from Hoechst).

Sarcosinates, having the structure (3):

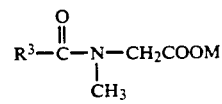

where
R$^3$ is chosen from $C_{6-14}$ alkyl, and

M is a counterion chosen from alkali metals, ammonium, substituted ammonium, such as alkanolammonium.

An example of sarcosinates having the structure (3), sodium lauryl sarcosinate (e.g. HAMPOSYL L-95, available from Grace).

Taurides, having the structure (4):

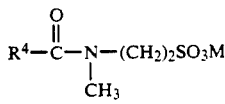

where
R$^4$ is chosen from C$_{8-18}$ alkyl

An example of taurides having the structure (4) is: coconut methyl taurine (e.g. FENOPON TC 42, available from GAF).

Isethionates, having the structure (5):

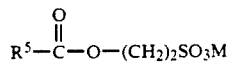

where
R$^5$ is chosen from C$_{8-18}$ alkyl.

An example of isethionates having the structure (5) is: sodium acyl isethionate (e.g. JORDAPON Cl, available from Jordan).

Monoalkyl sulphosuccinates, having the structure (6):

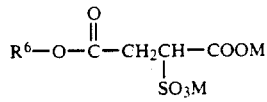

where
R$^6$ is chosen from C$_{10-20}$ alkyl.

Examples of monoalkyl sulphosuccinates having this structure (6) include:
sodium lauryl sulphosuccinate (e.g. EMPICOL SLL, available from Albright & Wilson)
magnesium alkyl sulphosuccinate (e.g. ELFANOL 616 Mg, available from AKZO),
sodium lauryl ethoxysulphosuccinate (e.g. EMPICOL SDD, available from Albright & Wilson)
coconut monoethanolamide ethoxysulphosuccinate, (e.g. EMPICOL SGG)
disodium lauryl polyglycolether sulphosuccinate (e.g. SURTAGENE S30, available from CHEM-Y)
polyethyleneglycol sulphosuccinate (e.g. REWOPOL SBFA 30, available from REWO).

Dialkyl sulphosuccinates, having the structure (7):

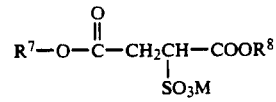

where
R$^7$ and R$^8$ are the same or different, and are chosen from C$_{6-14}$ alkyl.

An example of dialkyl sulphosuccinate having the structure (7) is:
sodium dioctyl sulphosuccinate (e.g. EMCOL 4500 available from Witco).

Acyl lactylates, having the structure (8):

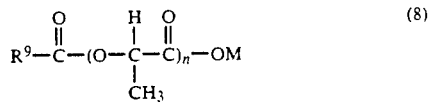

where
R$^9$ is chosen from C$_{6-16}$ alkyl.

An example of acyl lactates having the structure (8) is:
decanoyl lactate (e.g. PATIONIC 122A, available from Patterson, C.J.).
Acylated α-amino acids, such as sodium lauroyl glutamate (e.g. ACYLGLUTAMATE LS-11, available from Ajinomoto Co. Inc.).
Ethyl carboxylates, such as alkyl C$_{12-14}$O(EO)$_4$OCH$_2$CO$_2$Na (e.g. AKYPO RLM 38, available from AKZO).

Nonionic co-surfactants

A composition according to the invention can also comprise nonionic co-surfactants which are compounds produced by the condensation of alkylene oxide groups (hydrophilic in nature) with an organic hydrophobic compound, which may be aliphatic or alkyl aromatic in nature. Examples of nonionic co-surfactants include:
i. The polyethylene oxide condensates of alkyl phenols having from 6 to 12 carbon atoms, either straight or branched chain, with ethylene oxide, which is present in amounts of from 10 to 60 moles of ethylene oxide per mole of alkylphenol.
ii. The condensation product of aliphatic alcohols having from 8 to 18 carbon atoms, straight or branched chain, with ethyleneoxide, for example, a coconut alcohol ethyleneoxide condensate having from 10 to 13 moles of ethylene oxide per mole of coconut alcohol, the coconut alcohol fraction having from 10 to 14 carbon atoms.
iii. Long chain tertiary amineoxides having the structure (9):

where
R$^{10}$ contains an alkyl, alkenyl or monohydroxyalkyl radical of from 8 to 18 carbon atoms, from 0 to 10 ethylene oxide moieties and from 0 to 1 glyceryl moiety, and R$^{11}$ and R$^{12}$ contain from 1 to 3 carbon atoms and up to 1 hydroxy group, for example, methyl, ethyl, propyl, hydroxyethyl, or hydroxypropyl groups.

Especially preferred examples of nonionic cosurfactants include:
alkylethoxylates, such as the DOBANOL series, available from Shell;
esterethoxylates, such as the TAGAT series, available from Goldschmidt;
alkylalkanolamides, such as coconut monoethanolamide (e.g. EMPILAN CME, available from Albright & Wilson), and coconut diethanolomide, (e.g. EMPILAN CDE, available from Albright & Wilson).
sugar esters, such as sucrose laurate and methyl glucose laurate (available from Grillo-Werke A.G.)
esters of glycols, such as ethylene glycol mono stearate.
esters of glycerol, such as glyceryl mono stearate.
ethoxylated sorbitan esters, such as the TWEEN series (available from ICI).

amine oxides, such as alkyldimethyl amine oxide (e.g. EMPIGEN OB, available from Albright & Wilson) and alkylethoxydimethyl amine oxide (e.g. EMPIGEN OY, available from Albright & Wilson).

Zwitterionic and Amphoteric co-surfactants

The composition according to the invention can also contain zwitterionic co-surfactants, which are derivatives of aliphatic quaternary ammonium, phosphonium and sulphonium compounds in which the aliphatic radicals can be straight or branched chain, and where one aliphatic substituent contains from 8 to 18 carbon atoms, and one contains an anionic water-solubilising group, such as carboxyl, sulphonate, sulphate, phosphate or phosphonate.

Examples of zwitterionic co-surfactant include:
4-[N,N-di(2-hydroxyethyl)-N-octadecylammonio]butane-1-carboxylate, and
5-N,N-di(3-hydroxypropyl)-N-hexadecylammonio]-2-hydroxypentane-1-sulphate.

Particularly preferred zwitterionic co-surfactants are betaines, preferred examples of which are:
Alkyl betaines, having the structure (10):

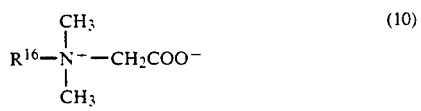

where
$R^{16}$ is $C_{10-16}$ alkyl.

An example of alkyl betaines having the structure (10) is:
lauryldimethyl betaine (e.g. EMPIGEN BB, available from Albright & Wilson).

Alkylamidopropyl betaines, having the structure (11):

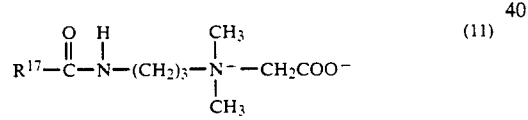

where
$R^{17}$ is $C_{10-16}$ alkyl.

An example of alkylamidopropyl betaines having the structure (11) is:
cocamidopropyl betaine (e.g. TEGOBETAIN L7, available from Goldschmidt).

Alkylamphoglycinates, and having the structure (12):

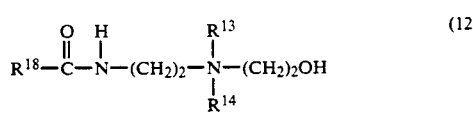

where
$R^{18}$ is $C_{10-16}$ alkyl
$R^{19}$ and $R^{20}$ are the same or different and are chosen from H, $CH_2COO^-$ and $(CH_2)_2COO^-$ An example of alkylamphoglycinates having the structure (12) is:
cocoamphoglycinate (available from GAF), and alkoamphodipropinate.

Sultaines, having the structure (13):

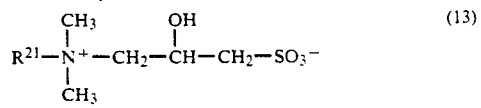

where
$R^{21}$ is chosen from $C_{12-16}$ alkyl or alkylamido.

An example of sultaines having the structure (13) is:
cocoamidopropylhydroxysultaine (e.g. CYCLOTERIC BET-CS, available from Alcolac).

Particularly preferred examples of amphoteric co-surfactants include:
Alkoamphoacetates, such as cocoamphoacetate (e.g. MIRANOL CM), and
Alkoamphopropionates, such as cocoamphopropionate (e.g. MIRANOL CM-SF)
both available from Miranol Inc.

The amount of co-surfactant when present in the compositions according to the invention is usually up to 50%, preferably from 1 to 40% by weight.

Optional thickening agent

The composition according to the invention can also comprise a polymer thickener in an amount sufficient to adjust the viscosity of the composition, so as to facilitate dispensing it conveniently onto the body surface.

Examples of polymer thickeners include:
anionic cellulose materials, such as sodium carboxy methyl cellulose;
anionic polymers such as carboxy vinyl polymers, for examples Carbomer 940 and 941;
nonionic cellulose materials, such a methyl cellulose and hydroxy propyl methyl cellulose;
cationic cellulose materials, such as Polymer JR 400;
cationic gum materials, such as Jaguar C13 S;
other gum materials such as gum acacia, gum tragacanth, locust bean gum, guar gum and carrageenan;
proteins, such as albumin and protein hydrolysates; and
clay materials, such as bentonite, hectorite, magnesium aluminium silicate, sodium magnesium silicate and a synthetic complex clay having the generic formula: $[Si_8Mg_{5.1}Li_{0.6}H_{4.6}O_{24}]^{0.6-}$ $Na^+_{0.6}$, an example of which is Laponite, available from Laporte Industries.

The amount of thickening agent which can optionally be employed in the composition according to the invention is normally from 0.05 to 5%, preferably 0.1 to 1% by weight of the composition.

Preservative

The composition according to the invention can also optionally comprise a preservative to prevent microbial spoilage, especially biodegradation of the alkyl phosphate salt. It is accordingly apparent that the composition containing the alkyl phosphate salt may be prone to attack by bacteria, moulds and fungi and other microbial influences. There is therefore a risk that the shelf-life of the composition might be unacceptably short due to the biodegradation or spoilage, unless there is included in the composition a bactericide, fungicide or other microbicide in an amount sufficient to inhibit or prevent the said biodegradation or spoilage, or unless other steps are taken to preserve the composition.

Examples of preservatives include:

(i) Chemical preservatives, such as ethanol, benzoic acid. sodium benzoate, sorbic acid, potassium sorbate, sodium propionate and the methyl, ethyl, propyl and butyl esters of p-hydroxybenzoic acid 2-bromo-2-nitro-propane-1,3-diol, phenoxyethanol, dibromodicyanobutane, formalin and Triclosan. The amount of chemical preservative optionally to be incorporated in the composition according to the invention will generally be from 0.05 to 5%, preferably from 0.1 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, sufficient should be incorporated in the composition according to the invention to reduce the water activity ($a_w$) from 1 to <0.9, preferably to <0.85 and most preferably <0.8, the lowest of these values being that at which yeasts, moulds and fungi will not proliferate.

Further optional ingredients

The composition according to the invention can also contain other optional adjuncts, that is ingredients other than the main ingredients already defined which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1,2-diol, butane-1,3-diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrate aluminium silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 50 to 98% by weight of the composition, and can, in the absence of other cosmetic adjuncts, form the balance of the composition.

PRODUCT FORM OF THE COMPOSITION

The composition according to the invention can take the form of a liquid or gel, intended to be dispensed from a capped container such as a bottle, roll-on applicator or tube, or a pump-operated or propellant driven aerosol dispenser, as a skin cleanser, shower product, bath additive or shampoo. The composition can also take for form of a powder or a solid such as a stick, preferably housed in a suitable capped holder with a wind-up or push-up action similar to a lip stick, or a bar or tablet, with or without fatty acid soaps, intended to be used for washing instead of a conventional soap bar.

The invention also provides a closed container containing a detergent composition as herein defined.

Process for Preparing the Composition

The invention also provides a process for preparing the composition of the type defined herein, which process comprises the steps of:

(i) preparing a mixture comprising one or more dialkyl and/or dialkenyl phosphate salts, as defined herein, and one or more monoalkyl and/or monoalkenyl phosphate salts, as defined herein, and (ii) subsequently packaging the mixture into containers.

Use of the composition

The composition according to the invention is intended primarily as a personal washing product for cleansing the face and other sensitive parts of the body surface, including the mucosae. It can also be used for washing the hair as well as the skin.

In use, a small quantity, for example from 1 to 5 ml, of the composition is either rubbed between the hands, together with water to form a foam, which is then used for washing, or applied via a flannel or sponge to the area to be cleansed, or the foam is generated directly on that area. The foam is subsequently rinsed away with clean water.

EVIDENCE TO SHOW ENHANCED LATHER PROPERTIES

Experiments were performed to demonstrate how lather volume obtainable with dioctyl phosphate salt increases with increasing levels of dilauryl phosphate salt and/or monolauryl phosphate salt in compositions according to the invention.

Foam was generated in a standard manner using a Foam Machine whose construction and use will now be described.

The Foam Machine

Foam is generated within a glass graduated cylinder by the action of a perforated piston upon the test composition and a suitably treated substrate. The repetitive compression and expansion of the substrate by the piston results in the aeration of the composition and the generation of foam which accumulates above the piston plate. The volume of the foam can then be read using the graduations of the cylinder when the piston is at its lowest point. The apparatus is enclosed and is supplied with air at a constant temperature of 38° C.

The operation of the machine in detail is as follows. Crimped nylon fibre is soaked in a large quantity of a solution of 2.5% by weight artificial sebum, consisting of squalene, cholesterol, long chain fatty acids, long chain triglycerides and decyl oleate, in dichloromethane for 1 hour. The solvent is poured away, and the fibres are dried by evaporation of residual solvent. The sebum-treated nylon fibre is intended to simulate greasy human skin or hair to which the composition of the invention would normally be applied when washing the skin or shampooing the hair.

Into a graduated glass cylinder of internal diameter 3.8 cm are placed two discs of polyurethane foam (diameter 3.8 cm, height 1.0 cm). 2 g of sebum-treated fibre is placed on top of the foam and the diluted test composition (2 ml) is poured over. The diluted composition is prepared from 7.5 g of test composition and 92.5 g of distilled water.

The prepared cylinder is placed within the foam machine, and with the crosshead at its lowest point the piston plate is adjusted to a level of 70 ml (as determined from the graduations on the cylinder).

The machine is operated with a periodicity of 12 rpm. After each minute of operation, the machine is stopped with the cross-head at the highest point and the volume of foam above the piston plate is recorded.

The machine is operated for a total of 10 minutes, the reported value is the mean of the foam volume values recorded between 3 and 10 minutes inclusive.

Foam Volume Results

All foam values for the mono- and di-alkyl phosphates were recorded for the triethanolamine salt at pH 8. The percentage surfactant in the composition is based on the weight of the mono- and di-alkyl phosphates in the acid form, not as the salt.

The following table shows the Foam Volumes obtainable from an aqueous solution containing mixtures of dioctyl phosphate (DOP), monolauryl phosphate (MLP) and dilauryl phosphate (DLP). Two weight ratios of MLP:DLP were tested; these were 60:40 and 75:25.

| MLP:DLP | MLP | DLP (% w/w) | DOP | Foam Volume (ml) |
|---|---|---|---|---|
| 60:40 | 9 | 6 | 0 | 0 |
| 60:40 | 9 | 6 | 1 | 33.1 |
| 60:40 | 9 | 6 | 2 | 45.7 |
| 60:40 | 9 | 6 | 5 | 51.4 |
| 60:40 | 9 | 6 | 10 | 44.6 |
| 60:40 | 9 | 6 | 15 | 52.0 |
| 60:40 | 9 | 6 | 20 | 50.0 |
| 75:25 | 11.25 | 3.75 | 0 | 0 |
| 75:25 | 11.25 | 3.75 | 1 | 28.3 |
| 75:25 | 11.25 | 3.75 | 2 | 52.3 |
| 75:25 | 11.25 | 3.75 | 5 | 50.9 |
| 75:25 | 11.25 | 3.75 | 10 | 52.3 |
| 75:25 | 11.25 | 3.75 | 15 | 54.3 |
| 75:25 | 11.25 | 3.75 | 20 | 52.6 |
| — | 0 | 0 | 20 | 46.3 |
| 100:0 | 15 | 0 | 0 | 53.7 |

From these results, it can be seen that the foam volume that can be generated from a mixture of monolauryl and dilauryl phosphate (on the triethanolammonium salts), where the "mono:di" weight ratio is less than that stipulated by Kao in their U.S. Pat. No. 4,139,485, is enhanced in the presence of added di-n-octyl phosphate salt. In fact, the foam volume that can be generated from a 60:40 weight ratio of MLP:DLP with added DOP is of the same order of magnitude as that obtainable using MLP alone.

EXAMPLES

The invention is further illustrated by reference to the following examples.

EXAMPLE 1

This Example illustrates a body cleansing liquid product suitable for use in the shower.

The product contains the following ingredients:

| Ingredients | % w/w |
|---|---|
| triethanolamine di-n-octyl phosphate | 18 |
| triethanolamine mono-n-lauryl phosphate | 18 |
| preservative | 2 |
| water to | 100 |

This product can be used for cleansing the whole body surface, including the hair, for example under the shower, a convenient amount of say 5 ml being placed in the palm of the hand prior to distributing over the body surface with added water to create a lather with superior volume and creaminess characteristics.

The properties of the above product were tested against another product containing only 36% by weight of triethanolamine mono-n-lauryl phosphate, the balance being water.

In this comparative test, strips of polyurethane foam were impregnated with equal quantities of the product according to the invention or the comparative product based on mono-n-luryl phosphate salt alone, each product first being diluted with tap water so that the concentration of alkyl phosphate in each case was 1% by weight.

Each member of a panel of twenty assessors was then asked to produce a foam by manually kneading one strip containing the mono-n-lauryl phosphate salt product and the other containing the di-n-octyl phosphate salt mono-n-lauryl phosphate salt mixture. Each panelist was then asked to decide which of the two samples gave the greater lather volume and the better lather creaminess. None of the panelists knew which sample was which.

The results of this test showed that the lather volume and lather creaminess of the product according to the invention containing both triethanolamine di-n-octyl phosphate and triethanolamine mono-n-lauryl phosphate was superior to that containing only the triethanolamine mono-n-lauryl phosphate, this difference being significantly different at the 95% level.

From this test it was concluded that the product according to the invention containing both the di-n-octyl phosphate salt and the mono-n-lauryl phosphate salt was superior to that containing only the mono-n-lauryl phosphate salt.

Examples 2 to 8 illustrate body shampoos for use in the shower or when bathing.

Examples 2 to 8 illustrate body shampoos for use in the shower or when bathing.

| Example 2 | % w/w |
|---|---|
| triethanolammonium dioctyl phosphate | 6 |
| triethanolammonium monolauryl phosphate | 18 |
| triethanolammonium dilauryl phosphate | 6 |
| triethanolammonium laurate | 1 |
| triethanolammonium myristate | 2 |
| lauryldimethylamine oxide | 2 |
| myristyldiethylamine oxide | 0.5 |
| cationised cellulose | 0.1 |
| propylene glycol | 10 |
| water to | 100 |

| Example 3 | % w/w |
|---|---|
| triethanolamine dioctylphosphate | 10 |
| triethanolamine monolauryl phosphate | 18 |
| triethanolamine dilauryl phosphate | 12 |
| lauryl dimethylbetaine | 3 |
| ethylene glycol monostearate | 1.5 |
| propylene glycol | 2.5 |
| preservative, perfume, dyes | q.v. |
| water to | 100% |

| Example 4 | % w/w |
|---|---|
| sodium di-(diethyleneglycol-mono-n-nonyl ether) phosphate | 10 |
| sodium mono-(diethyleneglycol-mono-n-nonyl ether) phosphate | 10 |
| sodium di-(diethyleneglycol-mono-n-lauryl ether) phosphate | 10 |
| triethanolammonium laurate | 1 |
| triethanolammonium myristate | 2 |
| alkyldialkylamine oxide (EMIGEN OB 30% active) | 8.3 |
| cationised cellulose | 0.1 |
| propylene glycol | 10 |
| water to | 100 |

| Example 5 | % w/w |
|---|---|
| triethanolammonium di-(ethyleneglycol-mono-n-octyl ether) phosphate | 20 |
| triethanolammonium mono-(ethyleneglycol-mono-n-octyl ether) phosphate | 8 |
| triethanolammonium di-(ethyleneglycol-mono-n-palmityl ether) phosphate | 10 |
| lauryl dimethylbetaine | 3 |
| ethylene glycol monostearate | 1.5 |
| propylene glycol | 2.5 |
| preservative, perfume, dyes | q.v. |
| water to | 100% |

| Example 6 | % w/w |
|---|---|
| triethanolammonium di-(ethyleneglycol-mono-n-heptyl ether) phosphate | 12 |
| triethanolammonium mono-(ethyleneglycol-mono-n-heptyl ether) phosphate | 15 |
| triethanolammonium di-(ethyleneglycol-mono-n-octadecyl ether) phosphate | 3 |
| triethanolammonium laurate | 1 |
| triethanolammonium myristate | 2 |
| alkyldialkylamine oxide (EMIGEN OB) 30% active) | 8.3 |
| cationised cellulose | 0.1 |
| propylene glycol | 10 |
| water to | 100 |

| Example 7 | % w/w |
|---|---|
| sodium di-(7-methyloctyl) phosphate | 18 |
| sodium mono-(7-methyloctyl) phosphate | 12 |
| sodium di-n-lauryl phosphate | 6 |
| lauryl dimethylbetaine | 3 |
| ethylene glycol monostearate | 1.5 |
| propylene glycol | 2.5 |
| preservative, perfume, dyes | q.v. |
| water to | 100% |

| Example 8 | % w/w |
|---|---|
| sodium di-(diethyleneglycol-mono-n-nonyl ether) phosphate | 10 |
| sodium mono-(diethyleneglycol-mono-n-nonyl ether) phosphate | 7 |
| sodium di-(diethyleneglycol mono-n-dodecyl ether) phosphate | 3 |
| cocamidopropyl betaine | 5 |
| preservatives, perfumes, dyes | q.v. |
| water to | 100 |

| Example 9 | % w/w |
|---|---|
| triethanolammonium diheptylphosphate | 20 |
| triethanolamine monomyristyl phosphate | 10 |
| cocamidopropyl betaine | 1.5 |
| preservatives, dyes, perfumes | q.v. |
| water to | 100% |

| Example 10 | |
|---|---|
| triethanolammonium dinonylphosphate | 10 |
| triethanolamine monodecyl phosphate | 10 |
| disodium lauryl sulphosuccinate | 4 |
| cocamidopropyl betaine | 4 |
| preservatives, dyes, perfumes | q.v. |
| water to | 100% |

| Example 11 | % w/w |
|---|---|
| triethanolammonium di-n-heptenyl phosphate | 10 |
| triethanolammonium mono-n-heptenyl phosphate | 10 |
| triethanolammonium di-n-lauryl phosphate | 10 |
| cocamidopropyl betaine | 1.5 |
| preservatives, dyes, perfumes | q.v. |
| water to | 100% |

| Example 12 | |
|---|---|
| triethanolammonium di-n-nonenyl phosphate | 10 |
| triethanolammonium di-n-myristenyl phosphate | 12 |
| triethanolammonium mono-n-nonenyl phosphate | 12 |
| disodium lauryl sulphosuccinate | 4 |
| cocamidopropyl betaine | 4 |
| preservatives, dyes, perfumes | q.v. |
| water to | 100% |

| Example 13 | % w/w |
|---|---|
| potassium di-(5-methylhexyl) phosphate | 15 |
| potassium mono-(5-methylhexyl) phosphate | 8 |
| potassium di-n-myristyl phosphate | 2 |
| cocamidopropyl betaine | 1.5 |
| preservatives, dyes, perfumes | q.v. |
| water to | 100% |

| Example 14 | % w/w |
|---|---|
| triethanolammonium di-(6,6-dimethylheptyl phosphate | 10 |
| triethanolammonium-mono-(6,6-dimethylheptyl) phosphate | 7 |
| triethanolammonium di-n-hexadecyl phosphate | 3 |
| disodium lauryl sulphosuccinate | 4 |
| cocamidopropyl betaine | 4 |
| preservatives, dyes, perfumes | q.v. |
| water to | 100% |

| Example 15 | % w/w |
|---|---|
| triethanolammonium di-octenyl phosphate | 8 |
| triethanolammonium mono-octenyl phosphate | 8 |
| triethanolammonium di-dodecenyl phosphate | 4 |
| lauryldimethyl betaine | 6 |
| preservatives, perfumes, dyes | q.v. |
| water to | 100 |

| Examples 16 | % w/w |
|---|---|
| triethanolammonium di-(7-methyloctyl) | 10 |

-continued

| phosphate | |
|---|---|
| triethanolammonium mono-(7-methyloctyl) phosphate | 10 |
| triethanolammonium di-lauryl phosphate | 5 |
| preservatives, perfumes, dyes | q.v. |
| water to | 100 |

Examples 17 to 21 illustrate facial foaming cleansers.

| Example 17 | % w/w |
|---|---|
| sodium dioctylphosphate | 15 |
| sodium monolauryl phosphate | 20 |
| sodium dilauryl phosphate | 13.3 |
| lauryl dimethyl betaine | 4 |
| sorbitol | 5 |
| glycerol | 2 |
| quaternised cellulosic polymer (Polymer JR400) | 0.3 |
| preservative, dyes, perfumes | q.v. |
| water to | 100 |

| Example 18 | % w/w |
|---|---|
| sodium di-(triethyleneglycol-mono-n-octenyl ether) phosphate | 12 |
| sodium mono-(triethyleneglycol-mono-n-octenyl ether) phosphate | 12 |
| sodium di-(triethyleneglycol-di-n-decenyl ether) phosphate | 4 |
| lauryl dimethyl betaine | 4 |
| sorbitol | 5 |
| glycerol | 2 |
| quaternised cellulosic polymer (Polymer JR400) | 0.3 |
| preservative, dyes, perfumes | q.v. |
| water to | 100 |

| Example 19 | % w/w |
|---|---|
| sodium di-n-octyl phosphate | 10 |
| sodium mono-n-octyl phosphate | 12 |
| sodium di-n-decyl phosphate | 8 |
| lauryl dimethyl betaine | 4 |
| sorbitol | 5 |
| glycerol | 2 |
| quaternised cellulosic polymer (Polymer JR400) | 0.3 |
| preservative, dyes, perfumes | q.v. |
| water to | 100 |

| Example 20 | |
|---|---|
| sodium di-n-octylphosphate | 5 |
| sodium di-n-nonylphosphate | 5 |
| sodium monomyristyl phosphate | 10 |
| sodium dimyristyl phosphate | 10 |
| sorbitol | 3 |
| preservatives, perfume, dyes | q.v. |
| water to | 100% |

| Example 21 | |
|---|---|
| sodium di-(diethyleneglycol-mono-n-octyl ether) phosphate | 10 |
| sodium mono-(diethyleneglycol-mono-lauryl ether) phosphate | 18 |
| sodium di-(diethyleneglycol-mono-lauryl ether) phosphate | 12 |
| sorbitol | 6 |
| propylene glycol | 2 |
| preservatives, perfumes, dyes | q.v. |
| water to | 100 |

EXAMPLES 22, 23 & 24

The following three examples illustrate soap-containing products with dioctyl phosphate salt and n-octanol in accordance with the invention.

In each case, the products were made in accordance with standard soap manufacture. The product of Example 22 yielded a flaked product which could not readily be pressed into a bar, as the flakes were not sufficiently cohesive. With the products of Examples 23 and 24, bars were formed following the usual plodding, extrusion and stamping that is conventional in soap bar manufacture.

These soap products had the following formulations:

| Ingredient | Examples 22 | 23 | 24 |
|---|---|---|---|
| | (% by weight) | | |
| Hardened Tallow Soap | 64 | 66.6 | — |
| 80/20 tallow-coco soap | — | 9 | 76 |
| sodium dioctyl phosphate | 12 | 18.4 | 17 |
| sodium monolauryl phosphate | 4 | 6 | 2 |
| water | 20 | 10 | 5 |

We claim:

1. An aqueous composition suitable for topical application to the skin or hair, which comprises:
  (a) from 1 to 99% by weight of a short chain dialkyl or dialkenyl phosphate salt (or mixtures thereof) having the structure (1):

$$R^{01}-(OCH_2CH_2)_a-O\underset{R^{02}-(OCH_2CH_2)_b-O}{\overset{O}{\diagup}}P-OX \quad (1)$$

(b) from 1 to 99% by weight of a monoalkyl or monoalkenyl phosphate salt (or mixture thereof), having the structure (2):

$$R^{03}-(OCH_2CH_2)_c-O-\underset{OZ}{\overset{O\quad OY}{\overset{\|\diagup}{P}}} \quad (2)$$

where
  $R^{01}$ and $R^{02}$ are each chosen from branched or unbranched alkyl or alkenyl groups having an average of from 7 to 9 carbon atoms;
  $R^{03}$ is chosen from branched or unbranched alkyl or alkenyl groups having an average of from 12 to 18 carbon atoms;
  X, Y and Z are each chosen from H, alkali metal, ammonium and substituted ammonium counterions; and a, b and c are each chosen from 0, or a value of from 1 to 4 and wherein the weight ratio of the monoalkyl or monoalkenyl phosphate salt to the short chain dialkyl or dialkenyl phosphate salt is from 9:1 to 1:2.3.

2. The composition of claim 1, wherein the short chain dialkyl phosphate moiety of the alkyl phosphate salt is selected from the group consisting of:
di-n-heptyl phosphate
di-n-octyl phosphate
di-n-nonyl phosphate
di-(7-methyloctyl) phosphate
di-(5-methylhexyl) phosphate
di-(6,6-dimethylheptyl) phosphate
di-(ethyleneglycol-mono-n-octyl ether) phosphate
di-(ethyleneglycol-mono-n-heptyl ether) phosphate
di-(diethyleneglycol-mono-n-nonyl ether) phosphate
n-hexyl-n-nonyl phosphate, and
n-hexyl-n-octyl phosphate.

3. The composition of claim 1, wherein the dialkenyl phosphate moiety of the alkenyl phosphate salt is selected from the group consisting of:

di-n-heptenyl phosphate
di-n-octenyl phosphate
di-n-nonenyl phosphate, and
di-triethyleneglycol-mono-n-octenyl ether)phosphate.

4. The composition of claim 1, wherein the dialkyl phosphate salt is a di-n-octyl phosphate salt.

5. The composition of claim 1, wherein the dialkyl or dialkenyl phosphate salt forms from 2 to 50% by weight of the composition.

6. The compositions of claim 1, wherein the monoalkyl phosphate moiety of the monoalkyl phosphate salt is selected from the group consisting of:
mono-n-decyl phosphate
mono-n-tetradecyl phosphate
mono-n-hexadecyl phosphate
mono-n-octadecyl phosphate
mono-(ethyleneglycol-mono-n-octadecyl ether) phosphate
mono-(diethyleneglycol-mono-n-octadecenyl ether) phosphate
mono-(polyethyleneglycol[5EO]-monooleyl ether) phospate, and
mono-(polyethyleneglycol[3EO]-monolauryl ether) phosphate.

7. The composition of claim 1, wherein the monoalkyl or monoalkenyl phosphate salt forms from 2 to 50% by weight of the composition.

8. The composition of claim 1, which further comprises a long chain dialkyl or dialkenyl phosphate salt (or mixtures thereof) having the structure (30):

$$R^{30}-(OCH_2CH_2)_d O\diagdown_{P-OX}^{O}$$
$$R^{31}-(OCH_2CH_2)_e O\diagup$$
(30)

where
R$^{30}$ and R$^{31}$ are each chosen from branched or unbranched alkyl or alkenyl groups having from 10 to 18 carbon atoms; and
d and e are each chosen from 0 or a value of from 1 to 10.

9. The composition of claim 8, wherein the long chain dialkyl phosphate moiety of the long chain dialkyl phosphate salt is selected from the group consisting of:
di-n-decyl phosphate
di-n-dodecyl phosphate
di-n-tetradecyl phosphate
di-n-hexadecyl phosphate, and
di-n-(polyethyleneglycol[3EO]-monolauryl ether) phosphate.

10. The composition of claim 8, wherein the long chain dialkenyl phosphate moiety of the long chain dialkenyl phosphate salt is selected from the group consisting of:
di-n-dodecenyl phosphate
di-(ethyleneglycol-mono-n-octadecenyl ether) phosphate
di-(diethyleneglycol-mono-n-octadecenyl ether) phosphate, and
di-(polyethyleneglycol[5EO]monooleyl ether) phosphate.

11. The composition of claim 1, wherein the salt is chosen from a sodium, a potassium or a triethanolamine salt.

12. The composition of claim 8, wherein the long chain phosphate salt forms from 1 to 10% by weight of the composition.

13. The composition of claim 1, which further comprises an anionic co-surfactant 14. The composition of claim 1, which further comprises a nonionic co-surfactant.

15. The composition of claim 1, which further comprises a zwitterionic co-surfactant.

16. The composition of claim 1, which is a liquid or gel product.

17. The composition of claim 1 which is a shampoo.

18. The composition of claim 1 which is a powder.

19. The composition of claim 1 which is a bar or tablet suitable for washing the skin.

20. A process for preparing the composition as claimed in claim 1, which process comprises the steps of:

1. preparing a mixture comprising:
    a. one or more dialkyl or dialkenyl phosphate salts having the structure (1):

$$R^{01}-(OCH_2CH_2)_a-O\diagdown_{P-OX}^{O}$$
$$R^{02}-(OCH_2CH_2)_b-O\diagup$$
(1)

b. one or more monoalkyl or monoalkenyl phosphate salts having the structure (2):

$$R^{03}-(OCH_2CH_2)_c-O-P\diagup^{O}_{\diagdown OZ}^{\phantom{O}OY}$$
(2)

where
R$^{01}$ and R$^{02}$ are chosen from branched or unbranched alkyl or alkenyl groups having an average of from 7 to 9 carbon atoms;
R$^{03}$ is chosen from branched or unbranched alkyl or alkenyl groups having an average of from 12 to 18 carbon atoms;
X, Y and Z are each chosen from H, alkali metal, ammonium and substituted ammonium counterions; and
a, b and c are each chosen from 0 or a value of from 1 to 4 and wherein the weight ratio of the monoalkyl or monoalkenyl phosphate salt to the short chain dialkyl or dialkenyl phosphate salt is from 9:1 to 1:2.3 ii. subsequently packaging the composition so formed into containers.

21. A method of cleansing the skin or hair which comprises the step of applying thereto an effective amount of the composition of claim 1, together with water, to form a foam, and subsequently rinsing the foam with water.

* * * * *